United States Patent
Jain et al.

(10) Patent No.: US 8,698,226 B2
(45) Date of Patent: Apr. 15, 2014

(54) SEMICONDUCTOR DEVICES, METHODS OF MANUFACTURE THEREOF AND ARTICLES COMPRISING THE SAME

(75) Inventors: Faquir C. Jain, Storrs, CT (US); Fotios Papadimitrakopoulos, West Hartford, CT (US)

(73) Assignee: University of Connecticut, Farmington, CT (US)

(*) Notice: Subject to any disclaimer, the term of this patent is extended or adjusted under 35 U.S.C. 154(b) by 780 days.

(21) Appl. No.: 12/533,770

(22) Filed: Jul. 31, 2009

(65) Prior Publication Data
US 2010/0025660 A1 Feb. 4, 2010

Related U.S. Application Data

(60) Provisional application No. 61/137,515, filed on Jul. 31, 2008.

(51) Int. Cl.
*H01L 29/788* (2006.01)
(52) U.S. Cl.
USPC .................................. 257/317; 257/E21.209
(58) Field of Classification Search
USPC ......................................... 257/317, E21.209
See application file for complete search history.

(56) References Cited

U.S. PATENT DOCUMENTS

| | | | | |
|---|---|---|---|---|
| 7,851,294 | B1* | 12/2010 | Basco et al. | 438/211 |
| 2004/0104129 | A1* | 6/2004 | Gu et al. | 205/775 |
| 2005/0047244 | A1* | 3/2005 | Rueckes et al. | 365/222 |
| 2006/0220094 | A1* | 10/2006 | Lojek | 257/315 |
| 2007/0014151 | A1* | 1/2007 | Zhang et al. | 365/185.01 |
| 2007/0132043 | A1* | 6/2007 | Bradley et al. | 257/414 |
| 2009/0173934 | A1* | 7/2009 | Jain | 257/20 |

OTHER PUBLICATIONS

R.H. Baughman, et al. "Carbon Nanotubes—the Route Toward Applications" Science's Compass Review (Aug. 2, 2002); pp. 787-792; vol. 297; Science (www.sciencemag.org).
C.Berger, et al. "Multiwalled Carbon Nanotubes are Ballistic Conductors at Room Temperature" Appl. Phys. A. (2002) pp. 363-365; vol. 74; Applied Physics A. Materials Science & Processing.
R. Croce, et al. "Carbon Nanotube Based Metal Oxide Semiconductor (MOS) Biosensor" 18thCMOC Symposium Proc. (Mar. 11, 2009) pp. 62-63, Yale University, New Haven CT.
E.K. Heller, et al. "Simulation of One-Dimensional Ring Quantum Interference Transistors Using the Time-Dependent Finite-Difference Beam Propagation Method" Journal of Applied Physics (Jun. 2000) pp. 8080-8087.
C. Faugeras, et al. "Epitaxially-Grown Graphite on Silicon Carbide, Pyrolitic Graphite and Graphene: a Raman Scattering Study" (Sep. 19, 2007) arXiv:0709.2538v3 [cond-mat.mes-hall]; arxiv.org.

(Continued)

*Primary Examiner* — Steven J Fulk
(74) *Attorney, Agent, or Firm* — Cantor Colburn LLP

(57) ABSTRACT

Disclosed herein is a device comprising a source region, a drain region and a gate layer; the source region, the drain region and the gate layer being disposed on a semiconductor host; the gate layer being disposed between source and drain regions; the gate layer comprising a first gate-insulator layer; a gate layer comprising carbon nanotubes and/or graphene. Disclosed herein too is a method comprising disposing a source region, a drain region and a gate layer on a semiconductor host; the gate layer being disposed between the source region and the drain region; the gate layer comprising carbon nanotubes and/or graphene.

14 Claims, 9 Drawing Sheets

(56) References Cited

OTHER PUBLICATIONS

S.K. Islam, et al. "Terahertz Quantum Interference Transistors (QUIT) Using One-Dimensional Modfet-Type Electron Waveguides" Superlattices and Microstructures(1995) pp. 221-224; vol. 17; No. 2; Academic Press Ltd.

R. Ugajin, et al. "A Proposal of a Vacuum Micro Quantum Interference Transistor" Journal of Applied Physics (Jan. 1993) pp. 1-7; vol. 73 (1); American Institute of Physics.

S. Russo, et al. "Aharonov-Bohm Effect in Graphene" (Nov. 2007) Electronic Paper.

M.L.Sadowski, et al. "Magnetospectroscopy of Epitaxial Few-Layer Graphene" Solid State Communications (2007); pp. 123-125; vol. 143; Elsevier, Ltd.

R. Setya, et al. "Novel Nonvolatile Memory Using Carbon Nanotube Gate FET Structures" 18th CMOC Symposium Proc. (Mar. 11, 2009); pp. 51-52; Yale University, New Haven CT.

W.A. De Heer "Carbon Nanotubes: Structure and Transport in Nanotubes" Nature Materials (2002); pp. 153-154; vol. 1; Nature Publishing Group.

W.A. De Heer, et al. "Epitaxial Graphene" Solid State Communications (2007); pp. 92-100; vol. 143; Science Direct; Elsevier (www.sciencedirect.com).

Z.L. Wang, et al. "In situ Imaging of Field Emission From Individual Carbon Nanotubes and Their Structural Damage" Applied Physics Letters (Feb. 4, 2002); pp. 856-858; vol. 80, No. 5; American Institute of Physics.

* cited by examiner

SEMICONDUCTOR DEVICES, METHODS OF MANUFACTURE THEREOF AND ARTICLES COMPRISING THE SAME

CROSS-REFERENCE TO RELATED APPLICATIONS

This application claims priority to provisional application 61/137,515 filed on Jul. 31, 2008, the entire contents of which are hereby incorporated by reference.

BACKGROUND

This disclosure relates to semiconductor devices, methods of manufacture thereof and to articles comprising the same.

Metal-Oxide-Semiconductor field effect transistor (MOSFET) technology is the dominant electronic device technology in use today. Performance enhancement and cost reduction between generations of integrated circuits (ICs) is generally achieved by reducing the size of transistors in the ICs, resulting in an enhancement in transistor speed and increasing integrated transistor area density. This is generally referred to as transistor "scaling".

Ultra-large-scale integrated (ULSI) circuits generally include a multitude of transistors, such as more than one million transistors and even several billion transistors that cooperate to perform various functions for an electronic component. The transistors are generally complementary metal oxide semiconductor field effect transistors (CMOSFETs) that include a gate conductor disposed between a source region and a drain region. The gate conductor is provided over a thin gate oxide material or high-k material. Generally, the gate conductor can be a metal, a polysilicon, or polysilicon/germanium ($Si_xGe_{(1-x)}$) material that controls charge carriers in a channel region between the drain and the source to turn the transistor on and off. The transistors can be N-channel MOSFETs or P-channel MOSFETs.

In semiconductor-on-insulator (SOI) semiconductor-type devices, transistors such as MOSFETs, are built on the top surface of a SOI substrate. The substrate is doped to form source and drain regions, and a conductive layer is provided between the source and drain regions. The conductive layer operates as a gate for the transistor; the gate controls current in a channel between the source and the drain regions. As transistors become smaller, the SOI thickness of the transistor is scaled down to achieve superior short-channel performance.

As MOSFETs are scaled to channel lengths below 100 nanometers (nm), conventional MOSFETs suffer from several problems. In particular, interactions between the source and drain of the MOSFET degrade the ability of the gate to control whether the device is on or off This phenomenon is called the "short-channel effect" or SCE.

It is therefore desirable to design MOSFETs having channel lengths of less than 100 nanometers that do not display the degradation and provide desired threshold voltage operation. Metal gates are currently used in sub-35nm device along with high-k dielectric gate insulators.

SUMMARY

Disclosed herein is a device comprising a source region, a drain region and a gate layer; the source region, the drain region and the gate layer being disposed on a semiconductor host; the gate layer being disposed between source and drain regions; the gate layer comprising a first gate-insulator layer; a gate layer comprising carbon nanotubes and/or graphene; and a gate contact layer. In case of nonvolatile memories, a second gate-insulator layer is disposed between the first gate-insulator layer and a metal contact layer. In applications such as sensors, the carbon nanotube and/or graphene gate layer surface is chemically processed such that it interacts with species where detection is desired. Use of carbon nanotubes, due to the control of their work function, are disclosed as gate materials which can support desired threshold values as well as are compatible with high temperature processing needed following gate deposition.

Disclosed herein too is a method comprising disposing a source region, a drain region and a gate layer on a semiconductor host; the gate layer being disposed between the source region and the drain region; the gate layer comprising carbon nanotubes and/or graphene.

Disclosed herein too is a graphene channel field effect device which has front and back gates disposed between source and drain regions with their respective gate insulator layers. The conductivity type of the graphene channel is induced by applying an appropriate polarity and magnitude voltage to one of the gates while controlling the transistor behavior with voltage applied to the other gate. In this graphene transistor, the gate voltage polarity determines whether the device is n-channel or p-channel.

BRIEF DESCRIPTION OF THE FIGURES

Referring now to the figures, which are exemplary embodiments, and wherein the like elements are numbered alike.

DETAILED DESCRIPTION

Figure 1:
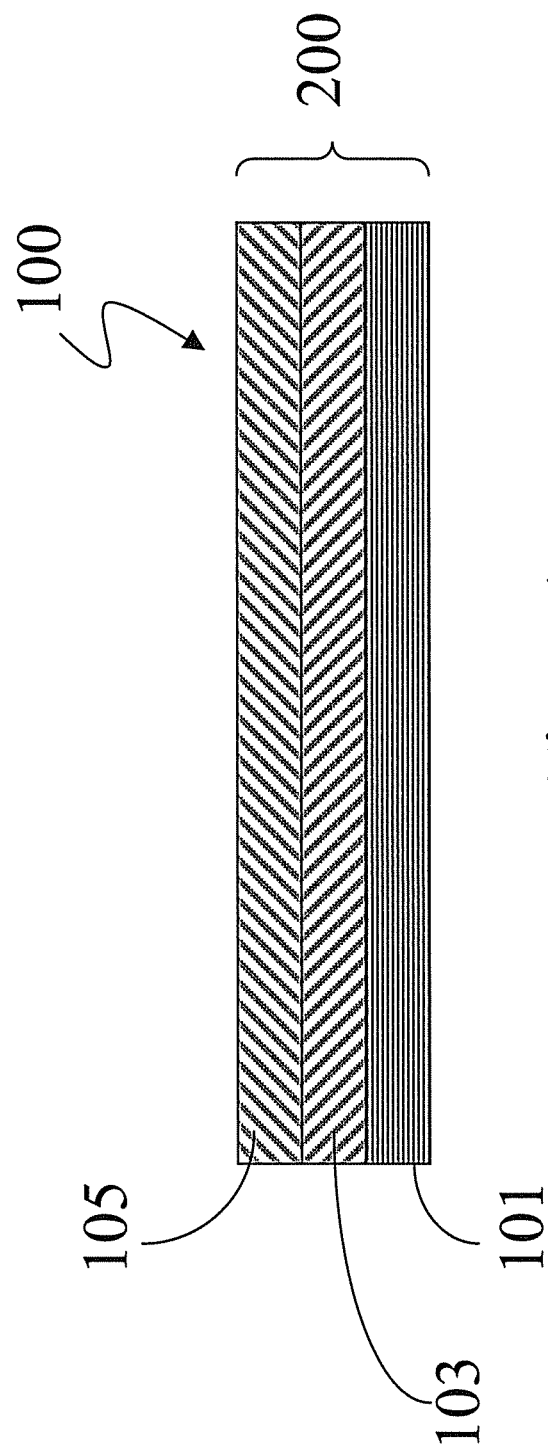
FIG. 1 depicts a semiconductor host comprising a wafer, an optional buried oxide layer and an optional SOI layer.

It will be understood that when an element or layer is referred to as being "on," "interposed," "disposed," or "between" another element or layer, it can be directly on, interposed, disposed, or between the other element or layer or intervening elements or layers may be present.

It will be understood that, although the terms first, second, third, and the like may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, first element, component, region, layer or section discussed below could be termed second element, component, region, layer or section without departing from the teachings of the present invention.

As used herein, the singular forms "a," "an" and "the" are intended to comprise the plural forms as well, unless the context clearly indicates otherwise. It will be further understood that the terms "comprises" and/or "comprising" when used in this specification, specify the presence of stated features, integers, steps, operations, elements, and/or components, but do not preclude the presence or addition of one or more other features, integers, steps, operations, elements, components, and/or groups thereof The transition phrases "comprising" may be substituted with the transition terms "consisting of" or the transition terms "consisting essentially of".

Disclosed herein are complementary metal oxide semiconductor field effect transistors (hereinafter "FETs") that use graphene sheets and/or carbon nanotubes as the gate layer disposed between a source region and a drain region over a thin gate insulator layer. The use of graphene sheets and/or carbon nanotubes as a gate layer permits the use of novel gates having a thickness of less than or equal to about 100 nanometers (nm), specifically less than or equal to about 90 nm, and more specifically less than or equal to about 35 nm, while minimizing or completely eliminating the short channel effect. In an exemplary embodiment, the use of graphene sheets and/or carbon nanotubes provides a route for manufacturing FETs that have a gate having a length of less than or equal to about 22 nm.

The approach is distinctly different from other commercial or conventional methods in which FETs are realized from the inclusion of carbon nanotubes. In these commercial or conventional methods silicon is invariably used as the gate material with silica ($SiO_2$) being used as the insulator. The use of carbon nanotubes and/or graphene as a gate layer provides one with the ability to obtain different work functions (e.g., using different weight ratios of metallic and semiconducting carbon nanotubes) for FETs. Carbon nanotubes can be separated into metallic, p-type or $p^+$ type or n-type nanotubes. Both metallic and semiconducting nanotube species can be chemically or electrically doped into p-type or $p^+$ type or n-type nanotubes. Doping of semiconducting nanotubes is more facile than metallic nanotubes. This provides flexibility of using them and achieving the desired threshold voltages that are needed in n-channel FETs and p-channel FETs. The method disclosed herein details the use of carbon nanotube-based FETs in place of metal gate silicon-germanium (SiGe) FETs (fully depleted devices or partly depleted devices).

The FETs comprising carbon nanotubes are advantageous in that they can be configured as nonvolatile memories with carbon nanotube floating gates. A floating gate is a layer in the gate region, which is sandwiched between two insulators and charge on the gate layer determines the state of the FET, "0" or "1". In one embodiment, the FETs with functionalized carbon nanotube or graphene gates can be used to detect biomarkers. In short, the FETs can be used as components of biosensors. Another advantage of the FETs is that they can be used as quantum interference transistors (QUIT) when graphene is used as the channel material. Gate layers comprising graphene and/or carbon nanotubes can be used in other FET material systems such as gallium arsenide (GaAs), indium gallium arsenide-indium phosphide (InGaAs—InP), silicon carbide (SiC) and gallium nitride (GaN) semiconductors. They can also be used in organic or polymeric semiconductors.

Figure 2:
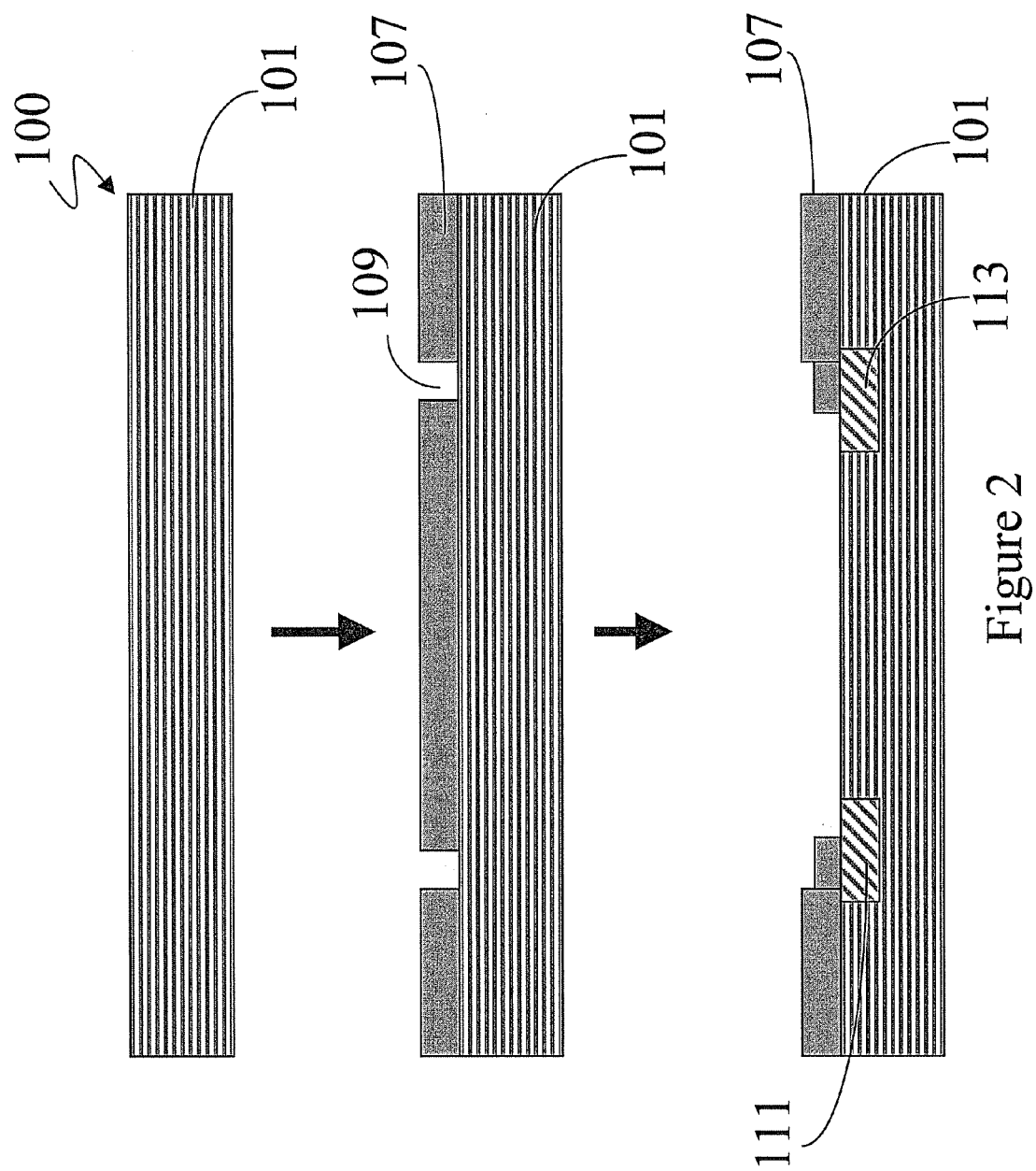
FIG. 2 depicts a method of manufacturing a FET that comprises a carbon nanotube and/or a graphene gate layer.
Figure 3:
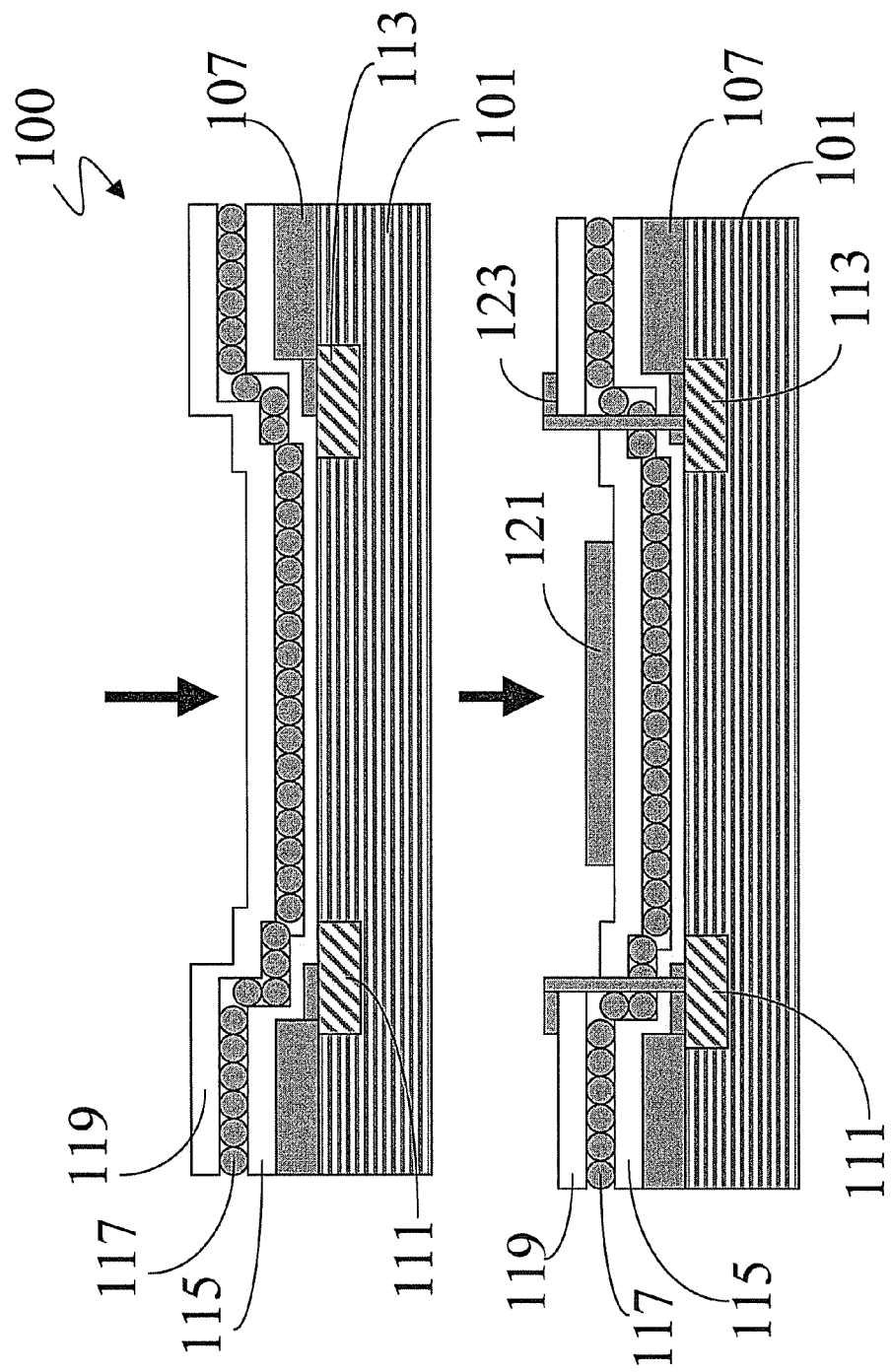
FIG. 3 is a continuation of FIG. 2, and further depicts the method of manufacturing a FET that comprises a carbon nanotube and/or a graphene gate layer.

FIGS. 1-3 will now be used to depict an exemplary method of manufacturing the FET device 100. It is to be noted that in the text as well as in all of the Figures, the respective structures will be termed the "device" and will be referred to by the number "100" though the device is not yet a FET device 100 till some of the last stages of manufacturing described herein. This is done primarily for the convenience of the reader.

With respect to the FIG. 1, a semiconductor host 200 comprises a wafer 101, an optional buried oxide layer 103 and an optional SOI layer 105 may be used as a starting point for the development of the device 100. Wafer 101 may comprise germanium, silicon, a combination of germanium and silicon such as silicon-germanium, gallium arsenide (GaAs), indium gallium arsenide-indium phosphide (InGaAs—InP), silicon carbide (SiC) or gallium nitride (GaN). In one embodiment, the wafer 101 may be doped with p-type dopant such as boron or an n-type dopant such as arsenic, phosphorus and gallium and annealed to activate the dopant. The wafer 101 may be doped to be effectively semiconducting. In an exemplary embodiment, the wafer 101 is a p-type doped silicon substrate.

The wafer 101 has an optional buried oxide (BOX) layer 103 disposed thereon. In one embodiment, the BOX layer 103 can comprise silicon dioxide produced by doping the silicon wafer 101 with oxygen as a dopant. An ion beam implantation process followed by high temperature annealing can be used to form a BOX layer 103. In another embodiment, the SOI wafer can be manufactured by wafer bonding, where the BOX layer 103 and the SOI layer 105 can be separately adhered to the wafer 101.

An optional silicon-on-insulator (SOI) layer 105 is disposed upon the BOX layer 103 and generally has a thickness of about 50 to about 200 nanometers. As depicted in the FIG. 1, the SOI layer is implanted with a p-type dopant or a n-type dopant such as those listed above.

FIGS. 2 and 3 depict one method of manufacturing the device 100. In the FIG. 2, a wafer 101 comprising silicon, p-type doped silicon, n-type doped silicon or a combination of silicon and germanium has a mask 107 of silicon nitride or silicon dioxide disposed thereon. Other materials such as organic materials and/or polymeric materials may also be used in the wafer 101 if desired. A window 109 in the mask permits the formation of a source region 111 and a drain region 113 respectively in the wafer 101. If the wafer 101 comprises a p-type dopant, the source region 111 and the drain region 113 are formed by doping the wafer 101 with a n-type dopant. Alternatively, if the wafer 101 comprises a n-type dopant, the source region 111 and the drain region 113 are formed by doping the wafer 101 with a p-type dopant.

A first gate-insulator layer 115 is then disposed upon the wafer 101 as shown in the FIG. 3. Following the disposing of the first gate-insulator layer 115 upon the wafer 101, a gate 117 that comprises graphene, carbon nanotubes or a combination of graphene and carbon nanotubes is disposed upon the gate insulating layer 115. Following the deposition of the gate, a second gate-insulator layer 119 may be disposed upon the gate 117. The gate 117 is therefore disposed between two gate-insulator layers 115 and 119. Examples of suitable insulators for the first gate-insulator layer 115 and/or the second gate-insulator layer 119 are materials having an energy band gap of greater than or equal to about 4.0 electron volts (ev), specifically greater than or equal to about 5.0 ev. Examples of gate-insulator materials are silicon nitride, silicon oxynitride, silica, hafnium oxide, organic materials, or polymeric materials having high-energy band gaps. Following the deposition of the second gate-insulator layer 119, the final metallization is conducted to manufacture the gate metal 121 and the source and drain interconnects 123.

The carbon nanotubes form a floating gate between the two gate-insulator layers. The carbon nanotubes that form the gate may be metallic or semiconducting carbon nanotubes. The nanotubes may be p-type or n-type carbon nanotubes. The resistivity of the carbon nanotubes can be used to control the magnitude of the threshold voltage and other electrical characteristics for a given gate-insulator layer thickness. The carbon nanotubes can be disposed upon the first gate-insulator layer 115 via a solution deposition process or via a vapor deposition process. The carbon nanotubes can be metallic or semiconducting single wall carbon nanotubes (SWNTs), double wall carbon nanotubes or multiwall carbon nanotubes (MWNTs).

In the solution deposition process, the device 100 comprising the wafer 101 having the source and drain regions contained therein and the first gate-insulator layer disposed 115 thereon, is contacted with a dispersion containing carbon nanotubes. The device 100 is sequentially contacted with a plurality of solutions. The first solution comprises an ionomer, the second solution comprises a salt while the third is a dispersion comprising carbon nanotubes. Each of these solutions is sonicated prior to contacting the device 100.

Each of the solutions is sonicated prior to being contacted with the device 100. The wafer 101 is first contacted with a mixture of sulfuric acid and hydrogen peroxide for a few seconds and rinsed in the deionized water before the assembly of the device 100 has started.

The device 100 comprising the wafer 101 having the source and drain regions contained therein and the first gate-insulator layer disposed 115 thereon, is contacted with the solution comprising the ionomer. Examples of the ionomer are ethanesulfonyl fluoride, 2-[1-[difluoro-[(trifluoroethenyl)oxy]methyl]-1,2,2,2-tetrafluoroethoxy]-1,1,2,2,-tetrafluoro- with tetrafluoroethylene, tetrafluoroethylene-perfluoro-3,6-dioxa-4-methyl-7-octenesulfonic acid copolymer both of which are commercially available under the trade name NAFION®. 5 weight percent Nafion solution was purchased from Aldrich chemicals, which contains aliphatic alcohol and water. The device 100 is immersed in the solution for a time period of about 5 minutes to about 100 minutes, specifically about 10 to about 20 minutes, and more specifically for about 15 minutes. The device 100 is then rinsed with deionized water.

The device 100 is then immersed in the second solution for a time period of about 5 minutes to about 100 minutes, specifically about 10 to about 20 minutes, and more specifically for about 15 minutes. The second solution (salt) contains iron chloride ($FeCl_3$) in deionized water. The second solution has a pH value 1.5 to 2.0, and more specifically 1.89. The device 100 is then rinsed with deionized water followed by a second rinse with dimethylformamide. Metallic nanotubes are rinsed in dimethylformamide, while semiconducting nanotubes are rinsed in tetrahydrofuran. When the carbon nanotubes are semiconducting, they are dispersed in tetrahydrofuran solution and the second rinse is conducted in tetrahydrofuran. There are methods to separate semiconducting nanotubes from metallic carbon nanotubes.

The device 100 is next immersed in a third solution that comprises semiconducting, metallic or a combination of semiconducting and metallic carbon nanotubes for a time period of about 5 minutes to about 100 minutes, specifically about 10 to about 20 minutes, and more specifically for about 30 minutes. The third solution comprises carbon nanotubes and dimethylformamide. Prior to adding the carbon nanotubes in dimethylformamide, the nanotubes are treated with sulfuric acid and nitric acid to attach a carboxyl (COOH) group at the end of carbon nanotubes. The device 100 is then rinsed with methanol and dried in air.

The gate layer comprising the carbon nanotubes is thus disposed upon the device 100. The gate layer 117 comprising the carbon nanotubes has a thickness of about 5 nanometers to about 100 nanometers, specifically about 6 to about 80 nanometers, and more specifically about 7 to about 50 nanometers. An exemplary thickness for the gate layer 117 is 10 micrometers. The nanotubes are aligned vertically in this methodology, i.e., they are arranged such that their longitudinal axes are substantially parallel to the upper surface of the first gate-insulator layer 115. However, other orientations can be used depending on the application. In the case of nonvolatile memory device, after the deposition of the carbon nanotubes, the second gate-insulator layer 119 is disposed upon the gate. The second gate insulator layer 119 is not needed in FETs. In one exemplary embodiment, the second gate insulator layer comprises $SiO_2$, $Si_3N_4$, SiON, where as the first gate insulator layer is $SiO_2$, $HfO_2$, and HfAlO.

In one embodiment, the gate layer 117 can comprise a combination of metallic carbon nanotubes and semiconducting carbon nanotubes. In one embodiment, the gate layer 117 may comprise up to about 100 wt % metallic carbon nanotubes, specifically up to about 80 wt % metallic carbon nanotubes, specifically up to about 60 wt % metallic carbon nanotubes, specifically up to about 40 wt % metallic carbon nanotubes, specifically up to about 20 wt % metallic carbon nanotubes, based upon the total weight of the gate layer 117. In another embodiment, the gate layer 117 may comprise up to about 100 wt % semiconducting carbon nanotubes, specifically up to about 80 wt % semiconducting carbon nanotubes, specifically up to about 60 wt % semiconducting carbon nanotubes, specifically up to about 40 wt % semiconducting carbon nanotubes, specifically up to about 20 wt % semiconducting carbon nanotubes, based upon the total weight of the gate layer 117.

The carbon nanotube gate layer 117 may also be disposed upon the first gate-insulator layer 115 by a vapor deposition process. In this process, catalytic metal particles or a layer of a catalytic metal is disposed upon the first gate-insulator layer 115 of the device 100. The device 100 is then placed in a furnace containing a carbonaceous gas at temperatures of 500 to about 1200° C. to produce a layer of carbon nanotubes that serve as the gate layer 117. Carbonaceous material methane in argon is used in one embodiment.

Examples of catalytic metals are transition metals and alloys thereof. Examples of transition metals that can be used as catalysts are iron, cobalt, nickel, gold, platinum, palladium, or the like, or a combination comprising at least one of the foregoing metals. The catalytic metals can be removed by high temperature vacuum annealing.

Examples of carbonaceous gases are benzene, toluene, xylene, cumene, ethylbenzene, naphthalene, phenanthrene, anthracene, methane, ethane, propane, ethylene, propylene or acetylene, methanol or ethanol, ketones such as acetone, and aldehydes such as formaldehyde or acetaldehyde, or the like, or a combination comprising at least one of the foregoing carbonaceous gases. The carbon nanotubes grown in this manner generally each have a longitudinal axis that is substantially perpendicular to the surface of the first gate-insulator layer 115.

Figure 4:
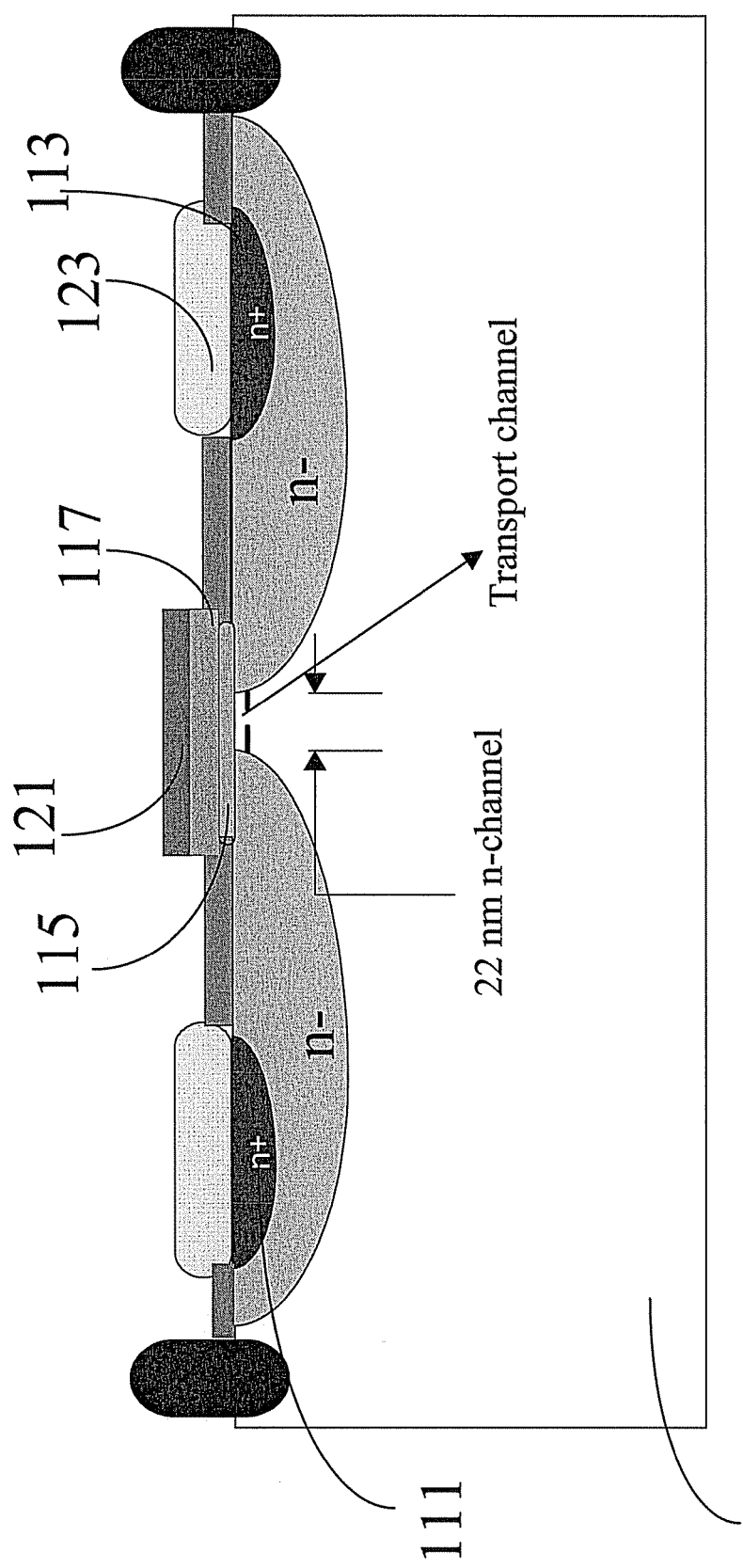
FIG. 4 is a depiction of a graphene and/or carbon nanotube gate layer with an asymmetric coupled quantum well increasing separation between the channel and the gate. This increased separation results in reduced tunneling.

In one embodiment, by using a mask having nanometer (less than or equal to about 100 nanometers) sized pores, nanometer sized catalytic islands may be patterned on the first gate-insulator layer. The device 100 containing these islands can then be introduced into the carbonaceous atmosphere contained in a furnace at temperatures of 500 to about 1200° C. Carbon nanotubes are generated form the patterned catalytic metal islands to form the gate layer 117. This gate layer 117 is therefore referred to as a self-assembled layer. An example of such a device 100 is depicted in the FIG. 4. FIG. 4 is a depiction of a graphene and/or carbon nanotube gate layer with an asymmetric coupled quantum well increasing separation between the channel and the gate. This increased separation results in reduced tunneling.

In yet another embodiment, the device 100 may be disposed in a furnace and a catalytic vapor such as ferrocene vapor may be subjected to carbonaceous vapors at temperatures of 500 to about 1200° C. to produce a layer of carbon nanotubes that are disposed upon the first gate-insulator layer 115 to serve as the gate layer 117. Any catalytic residue can be removed from the device 100 by vacuum annealing.

As noted above, the gate layer 117 may comprise a plurality of sheets of graphene that are stacked upon one another. The graphene sheets may be deposited on the first gate-insulator layer 115 by using scotch tape (exfoliation) or alternatively may be deposited from a vapor. The method of manufacturing graphene sheets from a vapor is described in de Epitaxial Graphene, Heer et al., Solid State Communications, 143(12), pages 92-100 (2007), the entire contents of which are hereby incorporated by reference. The graphene sheets can be doped with n-type dopants or p-type dopants by field effect doping in order to provide tunable work functions that can function in both n-channel and p-channel devices. In one embodiment, the graphene can be divided into small isolated regions serving as electrically isolated quantum dots, the quantum dot being charged by the transfer of carriers from the channel during a writing of a bit. The writing is achieved by the application of an appropriate gate voltage and drain region to source region voltage.

The gate layer 117 comprising the graphene has a thickness of about 2 nanometers to about 20 nanometers, specifically about 3 to about 15 nanometers, and more specifically about 7 to about 13 nanometers. An exemplary thickness for the gate layer 117 comprising graphene is 5 nanometers. In the case of nonvolatile memory device, after the deposition of the graphene, the second gate-insulator layer 119 disposed upon the gate. The second gate insulator is not used in a regular FET device.

In one embodiment, the carbon nanotubes and the graphene sheets used in the gate layer 117 can be functionalized to sense various chemicals including biomarkers. The carbon nanotubes can be functionalized to detect a protein, a peptide, an enzyme, an antibody, a nucleotide, an oligonucleotide, an antigen, an enzyme substrate, an enzyme inhibitor, a transition state analog of an enzyme substrate or a combination thereof The carbon nanotubes may be functionalized on either a sidewall, a hemispherical endcap or on both the side-wall as well as the hemispherical endcap. The carbon nanotubes and graphene can be uniformly or non-uniformly substituted. Functionalized carbon nanotubes or graphene can have the formula (I)

$$[C_nH_L]-R_m \quad (I)$$

wherein $C_n$ represents the surface carbons of a carbon nanotube. n is an integer, L is a number less than or equal to 0.1n, m is a number less than 0.5n, and wherein each of R is the same and is selected from $SO_3H$, COOH, $NH_2$, OH, R'CHOH, CHO, CN, COCl, COSH, SH, COOR', SR', $SiR_3'$, Si—(OR')$_y$—R'$_{(3-y)}$, R", $AlR_2'$, halide, ethylenically unsaturated functionalities, epoxide functionalities, or the like, wherein y is an integer equal to or less than 3, R' is hydrogen, alkyl, aryl, cycloalkyl, or araalkyl, cycloaryl, poly(alkylether), or the like, R" is fluoroalkyl, fluoroaryl, fluorocycloalkyl, fluoroaralkyl, cycloaryl, X is halide, and Z is a carboxylate or a trifluoroacetate. In one embodiment, these compositions are uniform in that each of R is the same. In another embodiment, these composition are not uniform in that each of R is different.

Also included are functionalized carbon nanotubes and graphene having the formula (II)

    (II)

where n, L, m, R' and R have the same meaning as above.

The substituted carbon nanotubes and graphene described above may advantageously be further functionalized. Such compositions include compositions of the formula (III)

    (III)

where the carbons are surface carbons of a carbon nanotube, n, L and m are as described above, A is selected from OY, NHY, —CR'$_2$—OY, N'Y, C'Y,

wherein Y is an appropriate functional group of a protein, a peptide, an enzyme, an antibody, a nucleotide, an oligonucleotide, an antigen, or an enzyme substrate, enzyme inhibitor or the transition state analog of an enzyme substrate or is selected from R'OH, R'NH$_2$, R'SH, R'CHO, R'CN, R'X, R'SiR'$_3$, RSi—(OR')$_y$—R'$_{(3-y)}$, R'Si—(O—SiR'$_2$)—OR', R'—R", R'—N—CO, (C$_2$H$_4$O)$_w$—Y, —(C$_3$H$_6$O)$_w$—H, —(C$_2$H$_4$O)$_w$—R', —(C$_3$H$_6$O)$_w$—R' and R', wherein w is an integer greater than one and less than 200.

The functional carbon nanotubes and graphene having the formula (II) may also be functionalized to produce carbon nanotubes having the formula (IV)

    (IV)

where n, L, m, R' and A are as defined above.

The carbon nanotubes and graphene may also have cyclic compounds adsorbed upon their surfaces. Examples of such carbon nanotubes are those having the formula (V)

    (V)

where n, L, m, and R are as defined above, a is zero or a number less than 10, X is a polynuclear aromatic, polyheteronuclear aromatic or an metallopolyheteronuclear aromatic moiety. Exemplary cyclic compounds are planar macrocycles, porphyrins, phthalocyanines.

The adsorbed cyclic compounds may be functionalized. Such compositions include compounds of the formula (VI)

    (VI)

where m, n, L, a, X and A are as defined above and the carbons are on the SWNT.

In the case of nonvolatile memory device, after disposing the carbon nanotubes and/or graphene on the first gate-insulator layer 115 to form the gate layer 117, a second gate-insulator layer 119 comprising silicon nitride, silicon oxynitride, silica, hafnium oxide, organic materials, or polymeric materials having high-energy band gaps may be disposed on the gate layer 117. Following the deposition of the second gate-insulator layer 119, the final metallization is conducted to manufacture the gate metal 121 and the source and drain interconnects 123. In FETs, the second gate insulator is not needed. Gate contacts (i.e., the source and drain interconnects) are formed on the carbon nanotubes or graphene layers.

FETs that comprise a carbon nanotube and/or a graphene gate layer are advantageous in that it can incorporate high mobility quantum well channels, a lightly doped sheath around the source and drain, along with conventional or lattice matched high-k dielectric as the gate insulator. The quantum well channel and the use of lattice matched gate insulators can be used in indium phosphide (InP) or gallium arsenide (GaAs) based FET structures. Lattice matched group II-VI gate insulators can be grown using low-temperature metallorganic chemical vapor deposition (MOCVD) or molecular beam epitaxial (MBE) methods.

Figure 6:
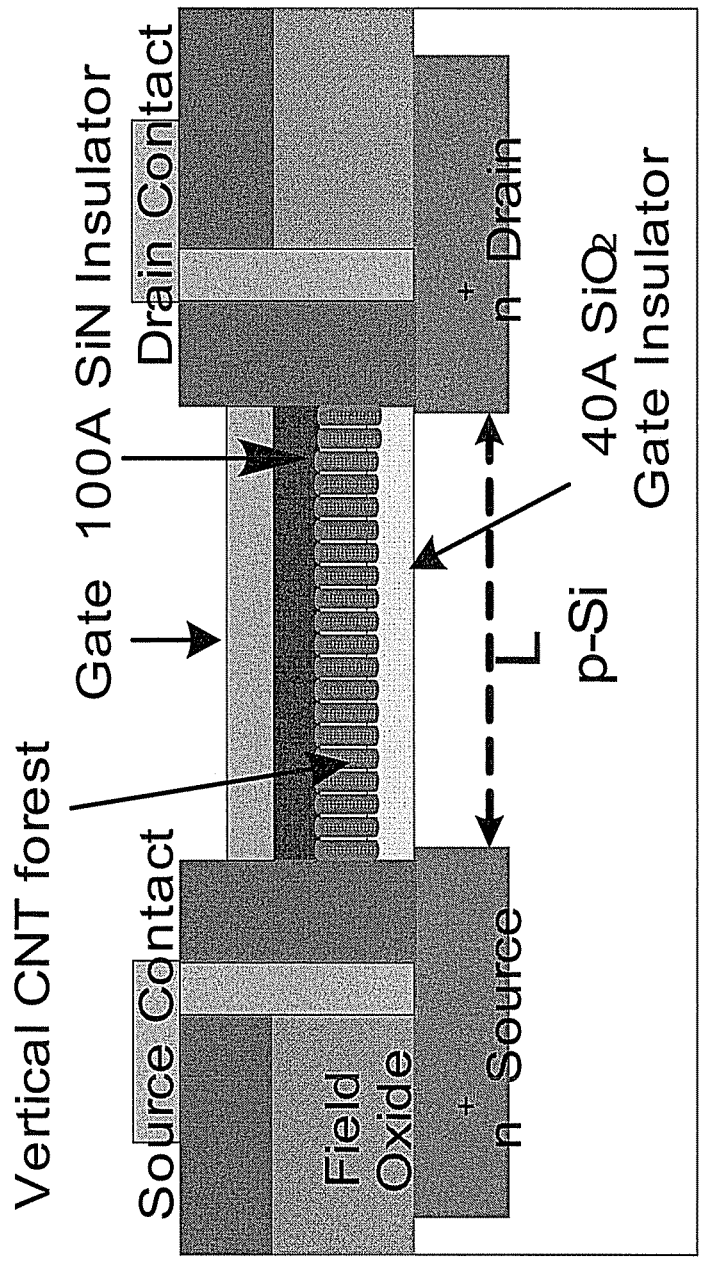
FIG. 6 is a depiction of the carbon nanotube gate layer FET used in the Example 1.

The device 100 can be configured as floating carbon nanotubes gate nonvolatile memory [see FIG. 6]. A graphene layer, configured as isolated nanosized discs, can be used as floating gate nonvolatile memory. In addition, as noted above, the functionalized carbon nanotube gate layers can be used as a nanosensor for bio-agent. In this embodiment the deposited carbon nanotubes are functionalized with HRP (horse radish peroxidase).

Figure 5:
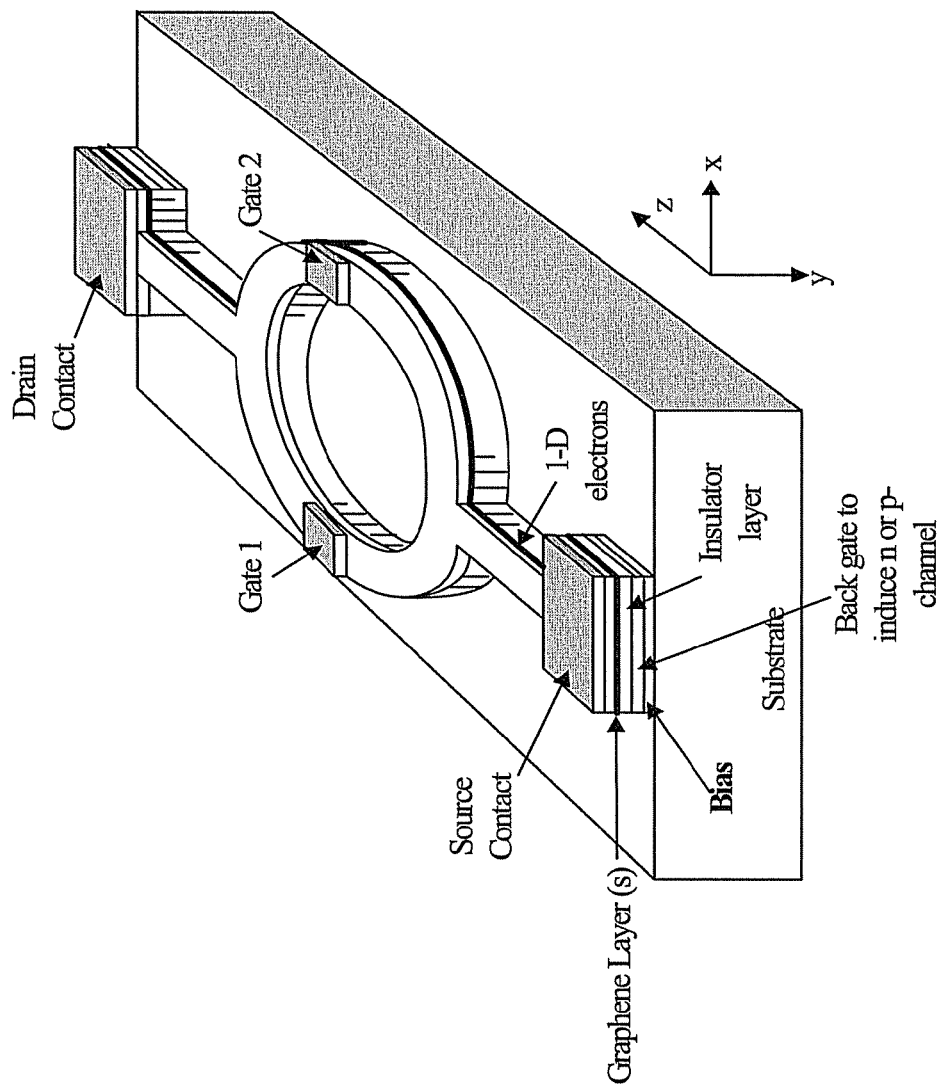
FIG. 5 depicts the use of the FETs in a quantum interference transistor. The quantum interference transistor uses graphene as the channel.

The FETs can also be used as quantum interference transistors. A quantum interference transistor using graphene as the channel is shown in FIG. 5. Here, with appropriate back gate bias an n-channel or p-channel is induced in the graphene transport channel layer. The front gates are used to modulate the carrier velocity and create interference, which turns the device ON and OFF. Note that in quantum interference transistors, the graphene replaces the semiconductor host in which transport channel is induced.

The device of FIG. 5, if implemented as having only one channel, will result in a graphene field-effect transistor (FET) structure in which one of the gates determines the channel conductivity type (n-channel or p-channel) and the other gate implements the transistor behavior by decreasing or increasing the channel current between source and drain region for a given drain to source voltage VDS. In this graphene transistor, one of the gates can be realized by having a carbon nanotube layer.

Carbon nanotube gate functionality depends on their work function. A FET's threshold voltage $V_{TH}$ depends on flat band voltage $V_{FB}$ and other parameters.

In one embodiment, the flat band voltage $$V_{FB} = \phi_{ms} - \frac{Q_{ox}}{C_{ox}},$$

where $Q_{ox}$ is the oxide charge (charge between the semiconductor surface and gate insulator and $C_{ox}$ is the gate insulator (oxide) capacitance per unit area. The work function difference between gate carbon nanotubes and p-Si (semiconductor host) is $\phi_{ms}$. It depends on the doping level of the semiconductor host where a transport inversion layer is formed, and work function of the carbon nanotubes or graphene. The work function of carbon nanotubes depends on their being metallic, p-semiconducting and n-type semiconducting. This in turn, depends on nanotube chirality.

$$\phi_{ms} = \phi_{CNT} - \phi_{p-Si}$$

$$V_{TH} = V_{FB} - \frac{Q_{sc}}{C_{ox}} + 2\psi_B$$

-continued $$\psi_B = \frac{kT}{q}\ln\left(\frac{N_A}{n_i}\right)$$

$$Q_{SC} = -qN_A W_M$$

where $W_m = \sqrt{\frac{2\varepsilon_{si}\varepsilon_o 2\psi_B}{qN_A}}$

Similarly in the case of graphene, the threshold voltage of a FET depends on its work function, which in turn depends if it has primarily electrons or holes. It has been shown in the literature [reference: J. R. Williams, L. DiCarlo, and C. M. Marcus, Quantum Hall Effect in a Gate-controlled p-n junction of graphene, Science, Vol. 317, pp. 637-640, 3 Aug. 2007] that field-effect biasing can cause n-type or p-type graphene behavior. Thus graphene and/or carbon nanotube gate layers are disclosed as alternate to currently used metal gates in sub-35 or smaller channel length FETs.

The following examples, which are meant to be exemplary, not limiting, illustrate the FETs and the methods of manufacturing of some of the various embodiments described herein.

EXAMPLES

Example 1

This example was conducted to demonstrate the drain current-gate voltage characteristics of a FET that has a gate layer manufactured from carbon nanotubes. This example also demonstrates how carbon nanotubes can be used to fabricate a nonvolatile memory device. The carbon nanotubes are single wall carbon nanotubes and they function as a floating gate. FIG. 6 is a depiction of the FET after manufacturing was completed. From the FIG. 6 it can be seen that the wafer comprised p-doped silicon upon which a 40 Angstrom (Å) silicon dioxide gate insulator was disposed. The carbon nanotubes were disposed upon the silicon dioxide gate insulator. A silicon nitride insulator having a thickness of about 100 Angstroms (Å) was disposed upon the carbon nanotubes. Alternately, a silicon dioxide layer can be grown as the second gate insulator.

A dense forest of carbon nanotubes is deposited by electrostatic interaction method. To get a negatively charged surface, the substrate is first immersed in the NAFION® solution. 5 weight percent Nafion solution was purchased from Aldrich Chemicals, which contains aliphatic alcohol and water. After that it is dipped into the ferric chloride solution resulting in the deposition of positively charged ferric ions onto the NAFION® layer (due to electrostatic attraction with the negatively charged sulfonate groups). The ferric chloride solution comprises iron chloride ($FeCl_3$) in deionized water with a pH value 1.5 to 2.0, and more specifically 1.89. The substrate was then immersed into DMF (dimethylformamide)-dispersed carbon nanotube solution for 3 hours.

Carbon nanotubes are prepared in dimethylformamide solution. Prior to adding carbon nanotubes in dimethylformamide, the nanotubes are treated with $H_2SO_4$ and $HNO_3$ mixture to attach COOH group at the end of carbon nanotubes. Consequently, negatively charged carbon nanotubes get deposited over the positively charged ferric ions. The carbon nanotubes were annealed at different temperatures in a vacuum.

The vacuum annealing was done with ramped temperature, e.g., 100° C. for 60 minutes, 300° C. for 60 minutes, 500° C.

for 60 minutes, followed by 300° C. for 60 minutes, 100° C. for 60 minutes, finally a cool down at 32° C. for 60 minutes.

Figure 7:
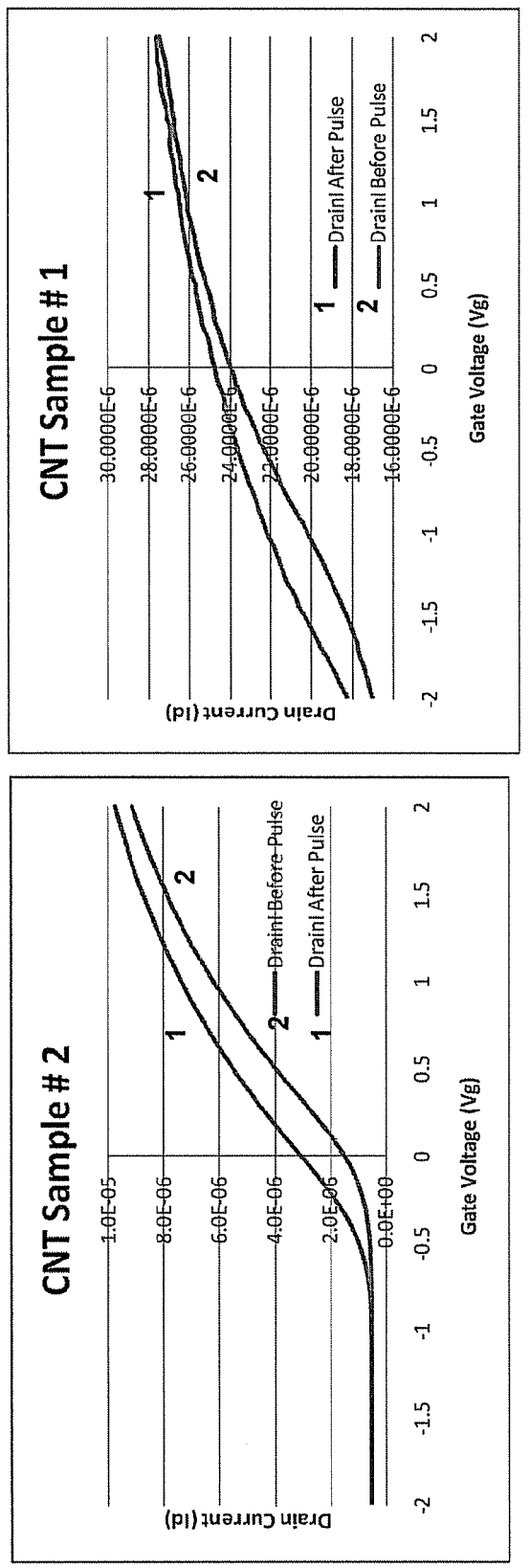
FIG. 7(a) is a drain current-gate voltage transfer characteristic (red before pulse) showing threshold shift (blue) after an electrical stress (writing pulse at drain)
FIG. 7(b) is a drain current-gate voltage transfer characteristic (red before pulse) showing threshold shift (blue) after an electrical stress (writing pulse at drain)

The comparative sample (i.e., control dielectric) is a thin layer of silicon nitride deposited using a Plasma Enhanced Chemical Vapor Deposition (PECVD) reactor. FIGS. 7(a) and 7(b) show the transfer $I_D$-$V_G$ characteristics of two devices. The threshold voltage shifts ($\Delta V_{TH}$)~0.5 V when the drain is stressed by a pulse of 20 V and 20 microseconds (μs) duration. During writing/programming, the channel electrons tunnel through the thin tunnel $SiO_2$ layer and are deposited on traps on the CNTs. The comparative samples have no CNTs and are prepared to determine the sites of electron trapping. CNT floating gate structures provide alternative routes to fabricate nonvolatile memory devices.

Example 2

The field of biosensing has recently been revolutionized with the advent and utilization of nanomaterials, specifically single wall carbon nanotubes (SWNTs). Carbon nanotubes have been employed in field-effect based biosensors due to their unique electrical and mechanical properties, which make for a fast, sensitive, and reliable sensing device.

This example was conducted to demonstrate the fabrication of a carbon nanotube gate metal oxide semiconductor biosensor, specific to the protein thrombin. In this device, the successful covalent attachment of a thrombin DNA aptamer, modified with an amine group, to a layer of carboxylated SWNTs located in the gate region is demonstrated.

Figure 8:
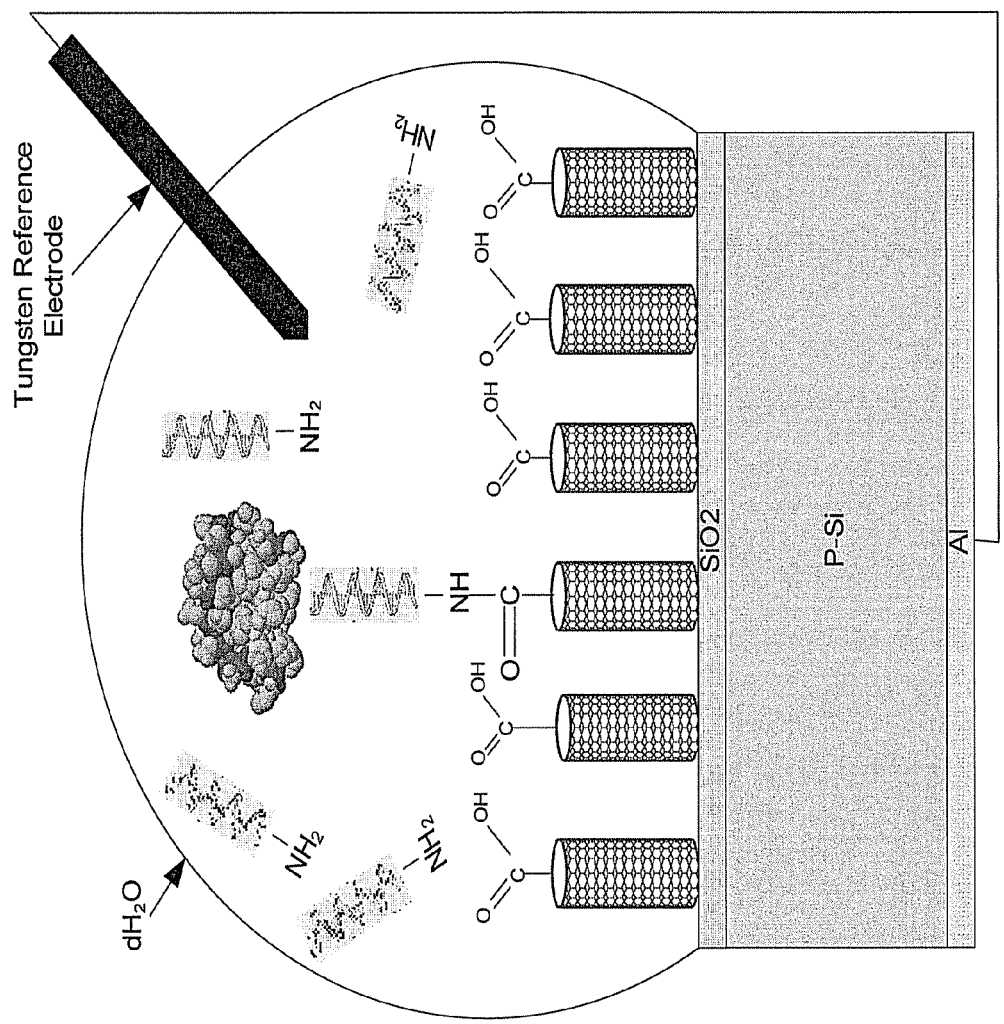
FIG. 8 is a cross-sectional schematic of a fabricated metal oxide semiconductor (MOS) device used in the detection of protein thrombin.

FIG. 8 is a cross-sectional schematic of a fabricated metal oxide semiconductor (MOS) device. The FIG. 8 depicts a MOS device comprising an aluminum substrate upon which is disposed a p-doped silicon layer. A silica layer is disposed upon the p-doped silicon layer. A tungsten electrode is in electrical communication with the aluminum substrate. Carboxyl functionalized carbon nanotubes are disposed upon the silica layer. A drop containing the thrombin DNA aptamer modified with an amine group is brought into the vicinity of the functionalized carbon nanotubes.

The small size of these aptamers facilitates successful detection because of the fact that the charge sensing can occur within the Debye length. It has been proven that the thrombin aptamer folds into a chair like quadruplex, with the adjacent 5' and 3' ends in the corner of the quadruplex, and two stacked G-quartets, which are linked with TT and TGT loops. Thrombin molecules are thought to bind adjacent to the TT loops.

Figure 9:
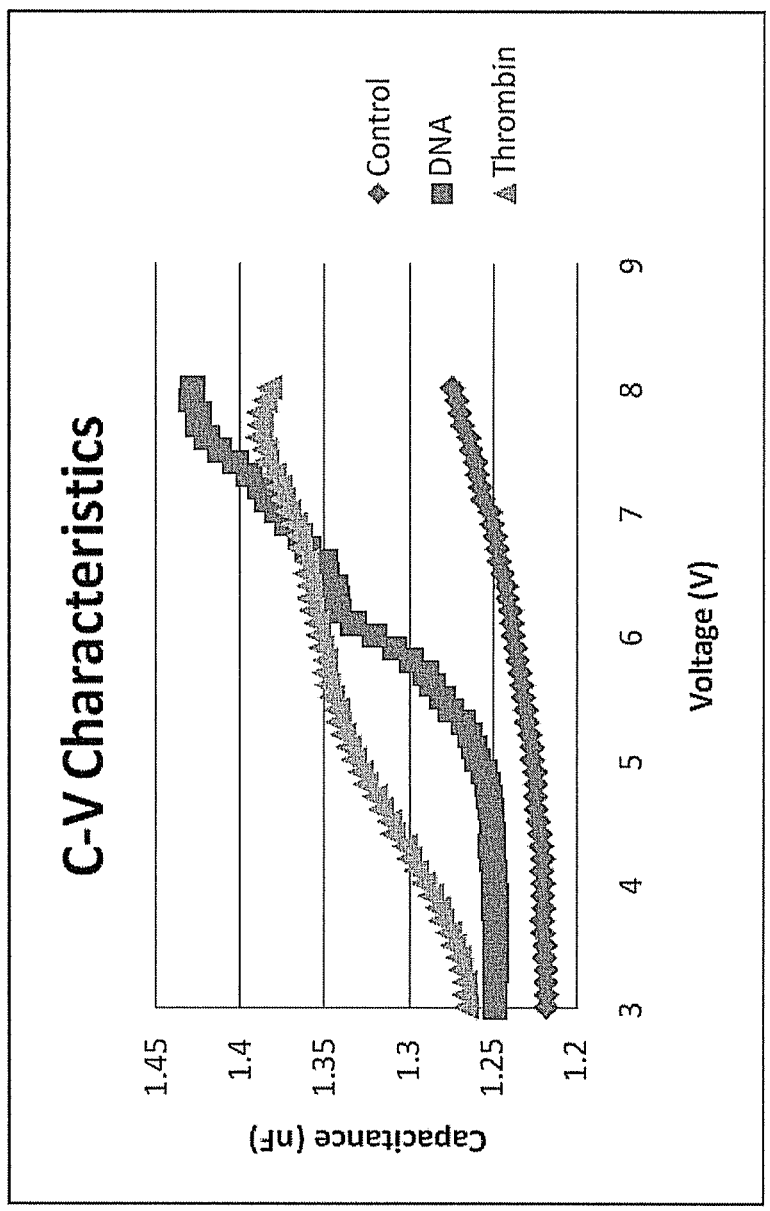
FIG. 9 shows capacitance-voltage characteristics of three samples: a control sample (without DNA aptamer and thrombin), with DNA functionalization to the carbon nanotubes, and attachment of DNA/thrombin complex.

FIG. 9 shows capacitance-voltage characteristics of three samples: a control sample (without DNA aptamer and thrombin), with DNA functionalization to the carbon nanotubes, and attachment of DNA/thrombin complex. Variations in the capacitance-voltage characteristics with and without thrombin are presented as evidence of successful detection.

While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A device comprising:
  a source region, a gate layer and a drain region; the source region, the gate layer and the drain region being disposed in a semiconductor host;
  the gate layer being formed between the source region and the drain region within the semiconductor host;
  the gate layer being surrounded by a thick insulator platform layer serving as a platform in which gate contacts are disposed;
  the gate layer between the source region and the drain region comprising a thin first gate-insulator layer above which is disposed a layer of graphene; the graphene layer contacting a first metal layer; the first metal layer contacting other devices to form a circuit;
  the first metal layer contacting the graphene layer is disposed on the thick insulator platform layer outside the active gate layer;
  a second gate-insulator layer being disposed on a surface of the graphene layer;
  a second metal layer contacting the second gate-insulator layer in the gate layer; the second metal layer and the first metal layer providing a bias to the graphene layer; the polarity of an applied bias across the second metal layer and the first metal layer determining the presence of n-type or p-type carriers and the electrical conductivity of the graphene layer serving as the gate layer, where a carrier type in graphene controls a magnitude of threshold voltage of the device.

2. The device of claim 1, where the semiconductor host is a p-type silicon, a n-type silicon, a germanium, a silicon-germanium, an organic material, a polymeric material or a combination comprising at least one of the foregoing materials.

3. The device of claim 1, where the first gate-insulator layer is silicon nitride, silicon oxynitride, silica, hafnium oxide, an organic material, a polymeric material or a combination comprising at least one of the foregoing materials.

4. The device of claim 1, where the second gate-insulator layer is silicon nitride, silicon oxynitride, silica, hafnium oxide, an organic material, a polymeric material or a combination comprising at least one of the foregoing materials.

5. The device of claim 1, where the graphene is p-type doped.

6. The device of claim 1, where the graphene is n-type doped.

7. The device of claim 1, disposed on a silicon-on-insulator substrate.

8. An article comprising the device of claim 1.

9. The article of claim 8, wherein the article is a field effect transistor.

10. The article of claim 1, wherein the article is a nonvolatile memory device.

11. The device of claim 1, where the graphene serves as the floating gate and forms a nonvolatile memory device, the graphene being divided into small isolated regions serving as electrically isolated quantum dots, the quantum dot being charged by the transfer of carriers from the channel during a writing of a bit, the said writing is achieved by the application of an appropriate gate voltage and drain region to source region voltage.

12. A field-effect transistor of claim 1, where the graphene layer is treated with to serve as the sensor gate electrode, the top surface of the graphene layer, deposited on a thin first insulator, is treated such as it permits deposition of DNA aptamers, catalysts comprising platinum, enzymes, that form a sensing gate, the said sensing gate being exposed to fluids consisting of target proteins and analytes, the said fluids are contacted by an electrode that connects the sensing transistor to the external circuits and biasing.

13. A field-effect transistor device configured as a quantum interference transistor, which comprises:
- two transport channels between source and drain regions; the transport channels being formed in a graphene layer; the graphene layer being disposed over a first insulating layer;
- the first insulating layer being disposed over a semiconductor layer; the semiconductor layer serving as a substrate as well as the back gate of the transistor; the graphene layer being contacted on opposing ends by metal layers forming the source regions and drain regions respectively;
- the first insulating layer having disposed thereon a layer of carbon nanotubes; the carbon nanotubes serving as a front gate layer; the front gate layer and the back gate layer providing a bias to the sandwiched graphene layer;
- the polarity of applied bias across the back gate layer determining the presence of n-type and p-type carriers and an electrical conductivity of the graphene layer serving as the transport channel of the quantum interference transistor; the voltage applied to the front gate controlling the electrical characteristics of the field-effect transistor for a given first gate insulator thickness.

14. A field-effect transistor device, which comprises:
- a transport channel between source and drain regions; the said transport channel is formed in a graphene layer; the said graphene layer is deposited over with an insulator layer selected from SiO2, HfO2, and other band gap materials which in turn is deposited over a semiconductor selected from Si, Ge, GaAs;
- the said semiconductor serving as the substrate as well as the back gate of the transistor, graphene gate layer is contacted on either end forming low resistance source and drain regions;
- the said graphene layer is deposited with a first thin insulator gate layer;
- the said first gate insulator layer is deposited with a layer comprising of carbon nanotubes or metallic layers forming the front gate of transistor;
- the said front gate layer and the back gate layer provides bias to the sandwiched graphene layer;
- the polarity of applied bias across one of the two gate layers determine the presence of n-type and p-type carriers and the electrical conductivity of the graphene layer serving as the transport channel of transistor; and
- the gate voltage applied across the other gate modulate the channel current for a given drain to source bias.

* * * * *